United States Patent [19]
Connolly

[11] Patent Number: 5,597,532
[45] Date of Patent: Jan. 28, 1997

[54] APPARATUS FOR DETERMINING SUBSTANCES CONTAINED IN A BODY FLUID

[76] Inventor: James Connolly, 8181 Morningside Dr., Indianapolis, Ind. 46240-2530

[21] Appl. No.: 326,788

[22] Filed: Oct. 20, 1994

[51] Int. Cl.[6] .......................... G01N 33/48; G01N 33/49
[52] U.S. Cl. ................... 422/58; 422/56; 422/61; 436/66; 436/164
[58] Field of Search ................. 422/56, 58, 61, 422/68.1; 436/66–68, 164

[56] References Cited

U.S. PATENT DOCUMENTS

| | | | |
|---|---|---|---|
| 3,723,064 | 3/1973 | Liotta | 23/230 |
| 4,199,261 | 4/1980 | Tidd | 356/448 |
| 4,199,550 | 4/1980 | Wielinger et al. | 422/58 |
| 4,446,232 | 5/1984 | Liotta | 435/7 |
| 4,472,353 | 9/1984 | Moore | 422/58 |
| 4,477,575 | 10/1984 | Vogel | 436/170 |
| 4,509,859 | 4/1985 | Markart | 356/446 |
| 4,523,853 | 6/1985 | Rosenbladt | 356/446 |
| 4,604,264 | 8/1986 | Rothe | 422/78 |
| 4,645,743 | 2/1987 | Baker et al. | 422/61 |
| 4,668,472 | 5/1987 | Sakamoto et al. | 422/58 |
| 4,676,653 | 6/1987 | Strohmeier | 356/446 |
| 4,729,657 | 3/1988 | Cooper | 356/319 |
| 4,797,473 | 1/1989 | Tarsio | 530/387 |
| 4,837,145 | 6/1989 | Liotta | 437/7 |
| 4,913,881 | 4/1990 | Evers | 422/58 |
| 4,952,373 | 8/1990 | Sugarman et al. | 422/61 |
| 4,987,085 | 1/1991 | Allen et al. | 422/61 |
| 5,049,487 | 9/1991 | Phillips | 435/4 |
| 5,059,394 | 10/1991 | Phillips | 422/68.1 |
| 5,104,619 | 4/1992 | de Castro | 422/56 |
| 5,135,716 | 8/1992 | Thakore | 422/56 |
| 5,139,685 | 8/1992 | de Castro | 210/767 |
| 5,166,051 | 11/1992 | Killeen | 435/7.1 |
| 5,179,005 | 1/1993 | Phillips | 435/14 |
| 5,212,060 | 4/1993 | Maddox | 435/7.1 |

Primary Examiner—Lyle A. Alexander
Attorney, Agent, or Firm—Jerrold J. Litzinger

[57] ABSTRACT

An apparatus for the optoelectronic evaluation of test paper strips for use in the detection of certain analytes in blood or other body fluids. The test strip comprises an elongated plastic part including a hinged portion to allow a first portion to be folded over a second portion. A series of layers of test strips are disposed between the folded over portions of the test strip. The test strip is configured such that the chemistry layers are placed in contacting engagement with one another, but not compressing one another. A reflectance photometer is provided and includes various features, including a lot number reader wherein if the test strip does not match the memory module, a test is not performed, and the user is instructed to insert a correct memory module.

20 Claims, 5 Drawing Sheets

APPARATUS FOR DETERMINING SUBSTANCES CONTAINED IN A BODY FLUID

BACKGROUND OF THE INVENTION

The present invention relates generally to an assay system for biological and nonbiological fluids. More particularly, the present invention relates to an apparatus for separating serum or plasma from particulate matter and then optoelectronically evaluating the serum or plasma in order to measure analytes within the serum.

It has long been desirable to utilize devices that can be used for on-site testing of blood products. Particularly important is the analysis of body fluids from humans and animals to diagnose disease, monitor the course of therapy, or determine the presence of illicit drugs. Commonly, the analytical methods used to carry out these objects are performed on blood samples.

Clinical chemists have a preference for working with serum over plasma and plasma over whole blood because of the clarity of the sample matrix and the lack of interfering substances from the solid portion of the blood. In order to facilitate analysis, a separation step must be carried out since the presence of red blood cells, either intact or hemolyzed interferes with the signal generated by the chemical reaction performed by the test.

Conventionally, the separation of blood components has been carried out by placing a blood sample in a centrifuge and centrifuging the sample for ten minutes at approximately 3,000 rpms. The serum obtained from this centrifuging step is then used to carry out the test, thus avoiding interferences from blood solids such as red blood cells.

An embodiment for chemical tests called dry reagent strips was developed first for urinalysis. Thereafter, various efforts to combine dry reagent strip technology in blood testing were started in the early 1950's. Notably, U.S. Pat. No. 3,092,465 discloses a reagent in a bibulous carrier with a superimposed semipermeable coating to exclude the chemical and nonchemical interferences from red blood cells. The device, while performing analysis on whole blood, still required additional manipulations by the user, in the form of washing of excess blood after a specified time interval. Additionally, U.S. Pat. Nos. 3,552,925 and 3,552,928 disclose the use of salts and amino acids to perform in-situ separation. U.S. Pat. No. 4,477,575 discloses the use of a glass fiber matrix.

More recently, membranes have been employed in a variety of devices. These include devices disclosed in the following United States and foreign patents and publications: U.S. Pat. Nos. 4,774,192 and 5,166,051; European Published Applications EP 0408222 A1, EP 0408223 A1, EP 0407800 A2 and EP 0388782; and PCT Published Applications Nos. WO 93/22453 and WO 90/10869. The use of the various membranes disclosed in the above patent documents operate on size exclusion principles, and several of these are limited by rates of capillary flow and do not completely eliminate interference from intact or hemolyzed red blood cells. Fresh red blood cells are elastic in nature and may pass through pores smaller than their nominal diameter. Hemolysis may occur on contact with some of the architectural or chemical components of the strips. Consequently, errors may be introduced into the measurement system.

U.S. Pat. No. 5,104,619 discloses a disposable diagnostic system comprising a test card having a substantially flat body and a generally cylindrical reagent pad pocket formed in a central area of the flat body. A reagent chemistry pad is disposed in the pocket and a snap fit cover is received in the pocket and arranged over the pad to retain the pad in position. The device size and configuration allows for bar code graphics to be printed on the underneath side of the device. The bar code may contain lot specified data about the reagent chemistry, and is read by the meter during device insertion. This data may further contain critical parameters for the software algorithm within the meter electronics. U.S. Pat. No. 5,139,685 also discloses a separation filter assembly having a snap fit lid. In this patent, glass fibers are utilized and maintained in a compressed state under pressure.

Accordingly, a need exists for an integrated system for assaying analytes and whole blood samples which are not affected by the chemical or physical interferences normally caused by red blood cells and other portions of whole blood.

SUMMARY OF THE INVENTION

The present invention, in one form thereof, comprises a dry solid phase diagnostic test strip and system for the chemical, enzymatic, and/or immunological analysis of whole blood analytes, comprising a reflectance photometer, a solid support strip, a porous detection zone member, a permeable spreading layer, an overlay sample receiving membrane containing an agent for the exclusion of intact red blood cells and a strip-receiving platform for positioning the strip inside the reflectance photometer. The detection area membrane may contain chemical, enzymatic, and/or immunological reagents that generate specific signals in the presence of a target analyte. The agent, in contact with the overlay membrane, prevents passage and hemolysis of red blood cells while facilitating rapid transport and reaction of the plasma or serum portion of introduced whole blood samples.

In addition, the present invention, in one form thereof, comprises a reflectance photometer which utilizes test strips that are color coded for test differentiation. For example, a blue strip may indicate a glucose test, whereas a red strip may indicate a cholesterol test. These colors are then divided into shades such as 64 shades of blue equal to 64 lot numbers of glucose strips. The photometer includes a separate optical read head that determines the color and shade of the base of the test strip device as the strip is inserted into the photometric instrument. The shade is converted into a lot number ranging from 1 to 64. The instrument also has a memory module (preferably an electrically erasable programmable read-only memory) that has a corresponding lot number to the shade of the strip to ensure lot number verification. The instrument then compares the inserted memory module programmed lot number to ensure that it is the same lot number as the test strip. If the strip lot number does not match the memory module lot number, the test is not performed, and the user is instructed to insert the correct memory module.

The lot number verification allows for the automated coding of lot numbers so that the user does not need to enter a lot code for each vial of strips. This prevents the running of the incorrect, old, or expired lot number tests in the instrument.

The "plug-in memory" of the module includes the lot number of the test strip, the expiration date, and the performance criteria for the actual strip measurement. The performance criteria include the wavelength, measurement algorithm, and unreacted density qualifications necessary for a valid test result.

The optoelectronic measurements of the chemistry test reaction on and in a surface enhances the dynamic range of the dry phase test. Algorithms that read at different wavelengths at different times in the chemistry reaction can extend the dynamic range of the test system. This is particularly applicable when using multiple chromophores in a single measurement system. The early portion of a chemistry could be read at the peak wavelength of a reaction, while the later portion or darker or more dense portion of color development could be read at a wavelength not near the peak of the color development. In addition, different chromophores may respond in a more linear manner in different portions of the dynamic range of the chemistry. Manipulation of these two data points can significantly increase the dynamic range (in mg/dl) of a chemistry reaction.

The optoelectronic measurement of the chemistry test reaction on and in a surface reduces error due to orientation of the surface to be read to the instrument. Multiple wavelengths and different angles are used to correct possible problems in positioning the strip in the instrument. If the detector is at "0" angle and the emitters of the same or different wavelengths are at different angles (e.g., one at 40° and one at 50°), the tilting of a surface will positively contribute to one reading while it will contribute in a negative manner to the other reading thus it is able to cancel the error presented by the angle presentation of the surface. These same measurement methods can be used to eliminate interferences from substances such as bilirubin and others.

The optoelectronic measurements of the chemistry test reaction on and in the surface enhance the stability of timed and untimed dry phase chemistry reaction. Algorithms are used to determine the "end point" of a chemistry. In other words, measurements can be done at similar or dissimilar wavelengths to predict the stable portion or end point of a chemistry. If kinetic measurements are made, the kinetic readings can be subjected to an algorithm to determine that the rate is slow enough to declare the extrapolate chemistry is at an end or completion. When known standards are run and predicted by this pseudo-endpoint, the same measuring criteria can be applied to unknowns to determine the "endpoint" of the test reaction.

The use of colored or shaded visual indicators in the instrument enhance the interpretation of test results. A colored bar graph is used to aid the user in knowing when the user test results are in a normal or safe range. Out of range colors such as orange for caution and red for danger are used when results are outside the green "safe" range. This is particularly useful to new testers who are not familiar with the number scale of the different test results. A voice module can also be used to warn the user of unsafe results or operation of the instrument system to make the system usable by the visually impaired by providing, for example, a sound beep for each unit of glucose during a glucose test.

DESCRIPTION OF THE PREFERRED EMBODIMENT

In accordance with the embodiment of the present invention, the diagnostic chemistry measurement device 10 for dry solid phase chemical, enzymatic, immunological assay of whole blood or sera analytes is made up of an injection molded carrier test strip 20 in which several porous and nonporous materials containing chemicals and reactants are contained for the purpose of generating a detectable signal in the presence of certain analytes. The test strip 12 is inserted into a reflectance photometer. The reaction material layer on the test strip 12 is held in intimate noncompressed contact with a whole blood separation layer in the absence of adhesives for the purpose of providing a liquid sample free of red blood cells to the reaction layer or layers.

HOLDER

Figure 2:
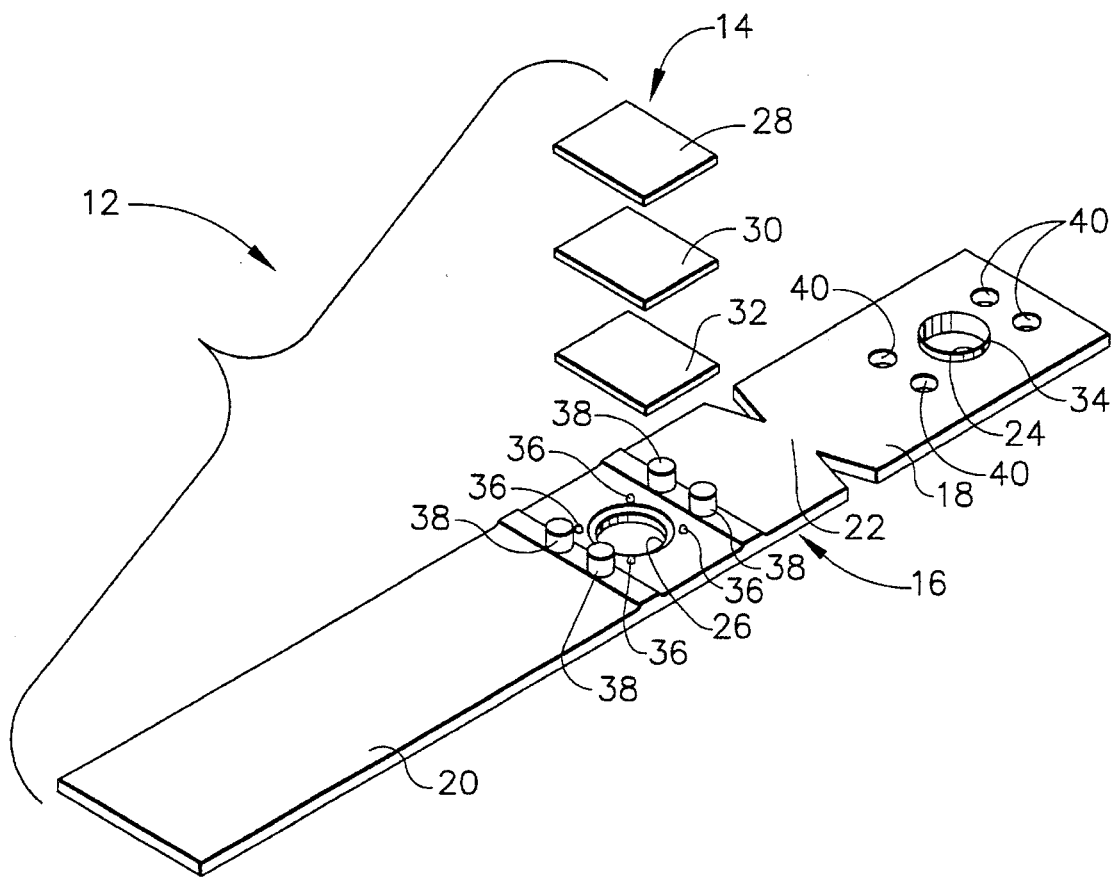
FIG. 2 is an exploded perspective view of the plastic test strip of present invention in its unlocked position.

The holder test strip 12 of this invention acts as holder for the different layers of the test reaction system. It provides a convenient handle as well as a mechanism for placing test strip 12 into an instrument 10 for the reading of the density changes of the reaction layers. As shown in FIG. 2 test strip 12 includes an elongate body 16 preferably formed by injection molding. Elongated body 16 includes a first end portion 18 and a second end portion 20. A hinged portion 22 is located between first and second and end portions 18 and 20 so that first end 18 is foldable over elongated body 16 into contact with second end 20.

Figure 3:
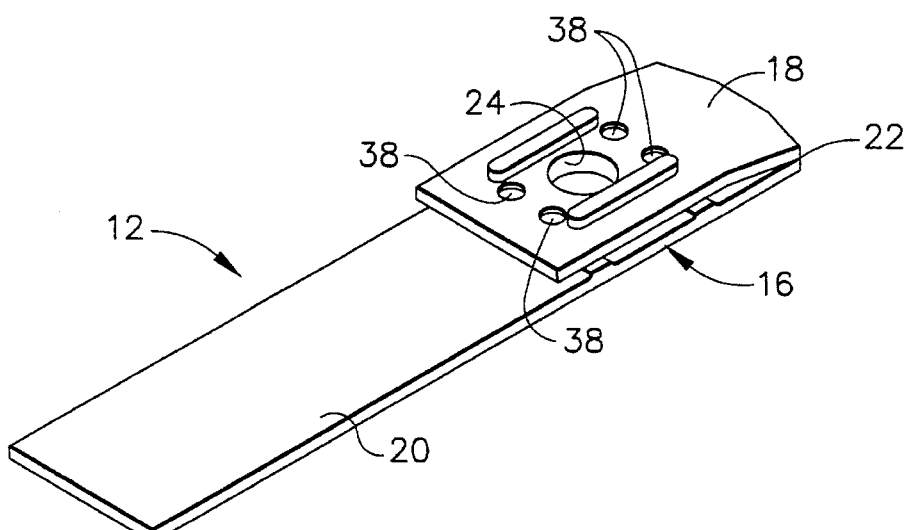
FIG. 3 is a perspective view of the plastic strip of FIG. 2 in its locked position.
Figure 4:
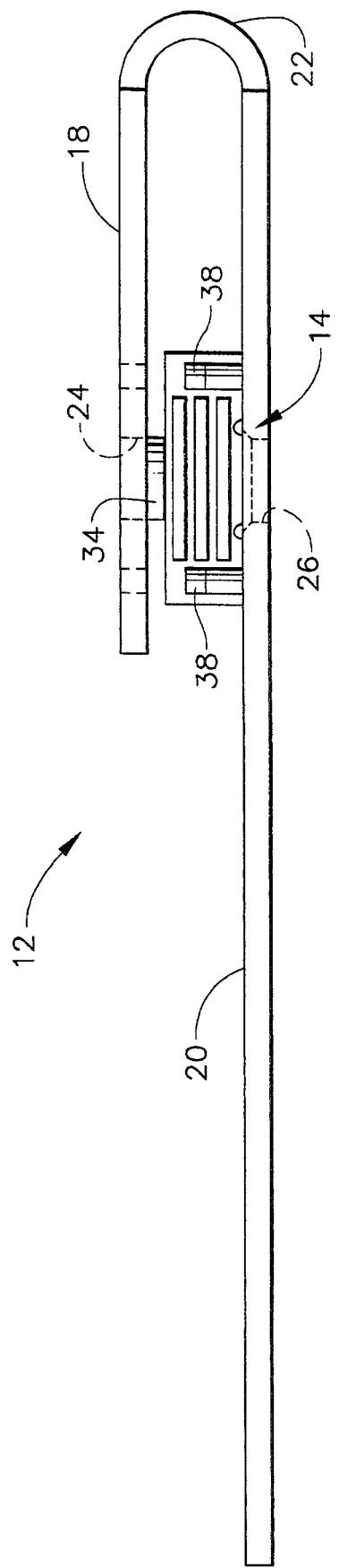
FIG. 4 is a sectional view of the plastic strip.

As shown in FIG. 2 first end portion 18 includes a opening 24 while second end portion 20 includes a complementary spaced opening 26. When first end portion 18 is folded over body 16, each opening 24 and 26 are aligned. In its folded position as shown in FIG. 3 opening 24 in test strip 12 defines an area for depositing a body fluid sample while opening 26 defines an area in which optoelectronic measurements of chemistry test reactions are conducted.

Test strip 12 further includes an adhesiveless carrier layer 14 formed from, for example, three particular layers. In a standard diagnostic test strip, carrier layer 14 may include a disbursement layer 28, formed of for example woven materials such as polyester or cotton, for rapid and even disbursement of body fluid along carrier layer 14. Beneath that may be included a separating layer 30 constructed of known materials such as shown in Table IX infra, that, when exposed to a sample liquid, may separate analyte and analyte disrupting elements such as red blood cells from whole blood. This action would permit the serum analytes to pass through separating layer 30 while preventing red blood cells or other analyte disrupting elements from passing through. The last layer shown in FIG. 2 is that of the test reaction membrane 32 on which the dry chemicals and reactants are contained for generating a visible signal in the presence of serum analytes. Molded carrier body 16 serves as a support for the reacting and nonreacting layers 28, 30 and 32 which may be formed from papers, membranes and deles materials.

The test strip holder 12 positions the different layer materials 28, 31, 32 within the holder the correct X, Y, and Z axis positions. Carrier layer 14 made up, for example, the disbursement separating and test reaction layers 28, 30 and 32 are held in noncompressed adhesiveless locations by first end portion 18 folding over to second end portion 20. This may be accomplished in a number of different ways. The preferred way of noncompressingly holding carrier layer is of an upstanding annular rim 34 may help locate the carrier layer 14 within test strip 12. Additionally, small upstanding protuberances 36 along second end portion 20, radially located away from opening 26 prevent movement of carrier layer 14. The purpose of both annular rim 34 and small upstanding protuberances 36 is to hold the layers of carrier layer 14 without compression between opening 24 and opening 26, thereby preventing pooling of any sample within carrier layer 14. This consideration of noncompression of the carrier layer 14 is of greater importance when larger numbers of layers are utilized. The positioning of a carrier layer 14 without adhesives or compression allows for efficient transport of sample and reactants contained in the system and test strip 12. Annular rim 34 or alternatively other areas of test strip 12 may include sawtooth protrusions to increase flow rate through carrier layer 14.

Test strip 12 includes a locking mechanism to prevent any unlocking of front end portion 18 from its folded position over elongated body 16. As shown in FIG. 2, one type of locking mechanism may include a plurality of upwardly extending tabs or projections 38 that interfit or lock into corresponding openings 40 in first end portion 18. When first end portion 18 is folded to second end portion 20, lock projections 38 will interfit and snap lock within openings 40. Other types of one way locking mechanisms may also be used, such as snap rivets.

More than one test reaction system can be housed in a test strip 12. A second set of holes 24, and 26 may be included in test strip 12 so that two tests may be run at once.

The described holding mechanism allows for the rapid separation of whole blood into its liquid and solid components. It also allows sample volumes as low 2.0 microliters to be used in dry phase chemistry reactions. Test strip 12 allows the use of several reaction and non-reaction layers. A typical holder could contain from 1 to 8 layers of material with thicknesses from approximately 0.002 inches to 0.007 inches, for example.

Chemicals and materials are employed to allow for the treatment of samples such as whole blood, which will allow the whole blood sample to be separated without disrupting the red blood cells while rapidly moving the liquid portion of the whole blood sample to one or more reaction sites in the holder, normally on a test reaction membrane 32. These chemicals can be composed of polymeric and nonpolymeric substances that are dried onto one or more surfaces of the materials contained in the device holder. Additionally, light metal salts of elements such as Potassium, Lithium, Sodium, and Calcium may be utilized to treat red blood cells before and during the separation process. The materials which may be used in the holder for treatment by or containment of these chemicals can be composed of woven, nonwoven, napped, or flocked materials.

ANALYTES

A wide variety of analytes can be determined by using the disclosed apparatus. Examples are given in tables I and II, infra.

Further, given the small size and robust nature of the reagent strips and instrumentation, analyses need not be limited to traditional clinical laboratory settings. The device of the present invention is also simple enough to be used by people with minimal or no chemical or medical technology training. This advantage allows use at home, or by mobile health care delivery people. Examples of this are diabetics that must monitor themselves for glucose and ketone bodies, patients on home dialysis who would benefit by monitoring of urea nitrogen and people endeavoring to lower their cholesterol levels.

Further, by combining several different reagents on a single support, a panel of tests may be done. Examples of this would be a liver panel consisting of ALT, AST, Alkaline Phosphates. A diabetic panel might consist of glucose, beta hydroxybutryrate and glycated hemoglobin. A coagulation panel might consist of Prothrombin time, ACTT, and ACT.

FAMILIES OF ANALYTES BY STRUCTURE

TABLE I

| Family | Examples |
| --- | --- |
| Carbohydrate | glucose, lactose, galactose |
| Nitrogen Moiety | urea nitrogen, creatinine, uric acid |
| Lipid | cholesterol, triglycerides, LDL, HDL |
| Enzyme | ALT, AST, Alkaline Phosphatase, CPK, CK-MB |
| Hormone | HCG, LH |
| Therapeutic Drugs | theophylline |
| Drugs of abuse | cocaine, marijuana, barbiturates, salicylates |
| Electrolyte | $Na^+$, $K^+$, $Cl^-$, $Li^+$, $CO^2$ |
| Nucleic Acids | infectious disease, forensic, applications, genetic disorders |

FAMILIES OF ANALYTES BY DISEASE

TABLE II

| Disease | Examples |
| --- | --- |
| Diabetes | glucose, beta hydroxybutyrate, hemoglobin $A_{1c}$ |
| Liver problems | ALT, AST, bilirubin |
| Acidosis/Alkalosi | $pO_2$, $pCO_2$, pH |
| Hypertension | $Na^+$, $K^+$ |
| Nutritional status | $Ca^{++}$, $Mg^{++}$, $Zn^{++}$, trace minerals |

EXAMPLES

The following illustrative examples teach various combinations of buffers, dyes, stabilizers and other reactive and functional components which may be combined by a person having ordinary skill in the art into the system test reaction areas.

Table IX gives various types of dyes and indicators used in diagnostic reagents.

EXAMPLE 1

Glucose measuring system

TABLE III

| Ingredient | Function | Amount | Available from |
| --- | --- | --- | --- |
| Glucose Oxidase | reactant | 25,000 | Sigma Chemicals, St. Louis, MO |
| Peroxidase | reactant | 75,000 | Sigma Chemicals, St. Louis, MO |
| Silwet 7500 | surfactant | 0.10 ml | Dow-Corning, Midland, MI |
| PVP K 30 | enzyme stabilizer | 0.50 gms | ISP, Linden, NJ |
| Citric Acid | Buffer | 1.25 gms | Aldrich Chemical, |

TABLE III-continued

| Ingredient | Function | Amount | Available from |
|---|---|---|---|
| Sodium citrate | system Buffer system | 0.10 ml | Milwaukee, WI Dow-Corning, Midland, MI |
| DOW 1520 | antifoam | 1.00 gms | Aldrich Chemical, Milwaukee, WI |
| 4 AAP | chromophore | 0.25 gms | Aldrich Chemical, Milwaukee, WI |
| 3,5 DCHBS | chromophore | 0.25 mgs | Boehringer Mannheim |
| Distilled $H_2O$ | solvent | QS to 100 ml | |

Preparation: Approximately 50 ml of distilled $H_2O$ was placed in a beaker on a stirring plate. A magnetic bar was added and the ingredients added sequentially after the previous gradient was dissolved and dispersed. After all ingredients were added the volume was adjusted to 100 ml of distilled $H_2O$.

EXAMPLE 2

Triglycerides measuring system

TRIGLYCERIDES+$H_2O$ $\xrightarrow{CHOLESTEROL\ ESTERASE}$ GLYCEROL+FREE FATTY ACIDS GLYCEROL+ATP $\xrightarrow{GLYCEROL\ KINASE}$ L–ALPHA–GLYCEROPHOSPHATE+$H_2O_2$ $H_2O^2$+ 4-AMINOANTIPYRINE+DCHBS $\xrightarrow{PEROXIDASE}$ QUINONEIMINE CHROMOPHORE

TABLE IV

| Ingredient | Function | Amount | Available from |
|---|---|---|---|
| Cholesterol esterase | reactant | 15,000 units | Shinko-American, N.Y., N.Y. |
| glycerol kinase | reactant | 5,000 units | Shinko-American, N.Y., N.Y. |
| glycerophosphate oxidase | reactant | 5,000 units | Shinko-American, N.Y., N.Y. |
| peroxidase | reactant | 5,000 units | Shinko-American, N.Y., N.Y. |
| 4 AAP | chromogen | 1.00 gm | Aldrich |
| 3, 5 DCHBS | chromogen | 0.25 gm | Boehringer Mannheim |
| MES | buffer | 2.50 gm | Research Organics |
| PVP K30 | stabilizer | 0.50 gm | ISP |
| glucose | filler | 2.50 gm | Sigma |
| triton X-100 | surfactant | 0.10 gm | Boehringer Mannheim |
| Distilled $H_2O$ | solvent | QS to 100 ml | |

Preparation: Same as example 1

EXAMPLE 3

Cholesterol measuring system (all amounts approximate)

TABLE V

| Ingredient | Function | Amount | Available from |
|---|---|---|---|
| Cholesterol Oxidase | reactant | 10,000 | Shinko-American, N.Y., N.Y. |
| cholesterol | reactant | 7,000 | Shinko-American, N.Y., N.Y. |
| sodium phosphate 0.5M pH 7.0 | buffer | 750 ml | Dow-Corning, |
| B.S.A. | surfactant | 15 gm | Aldrich Chemical, |
| peroxidase | reactant | 170,000 | Shinko-American, |
| DOSS | surfactant | 7.0 gms | Boehringer Mannheim |
| sucrose | stabilizer | 1.0 gms | Sigma Chemicals, |

TABLE V-continued

| Ingredient | Function | Amount | Available from |
|---|---|---|---|
| TMB | chromogen | 10.0 gms | Aldrich Chemical, |
| Distilled $H_2O$ | solvent | QS to 100 ml | |

Preparation: same as example 1

Alternatively, the chromogen may be prepared in an organic solvent matrix and treated as a first or 2nd application to the membrane or paper.

TABLE VI

| Ingredient | Function | Amount | Available from |
|---|---|---|---|
| Acetone/methanol 1:1 | Solvent | 100 ml | Aldrich |
| Tetramethyl benezidine | solvent chromogen | 1.00 gm | Biosynth Inc., Chicago, IL |

EXAMPLE 4

Blood Urea Nitrogen Measuring System

TABLE VII

| Ingredient | Function |
|---|---|
| Urease | reactant |
| $H_2O$ | solvent |
| Bcomthymol blue | chromogen |
| PVP K90 | film former |
| Fructose | filler |

Preparation: Same as experiment #1.

TABLE VIII

Types of Indicators

Chromogenic substrate

Redox

Leuco dyes

Oxidative couplers

Benzidene Derivatives

Fluorescent labels

Dye releasing system

TABLE IX

| Separation mechanisms used in dry reagents | | |
|---|---|---|
| Chemical | Physical | Mechanical |
| Dextran | hydrophilic polymers | centrifuge |
| sugars | porous latex films | filters |
| lectin | polymer & swelling agent | filters & pressure |
| amino acids | membranes | membranes & differential pressure |
| PEG/polyacrylate | microfiber cloth | wedge shape |
| thrombin | napped cloth | |
| gels | sintered porous matrix | |
| coagulants | density gradient | |
| agglutinating agents | glass fibers | |
| amine polymers | hollow fibers | |
| trivalent cations | membrane | |

SPECTROPHOTOMETER

Figure 1:
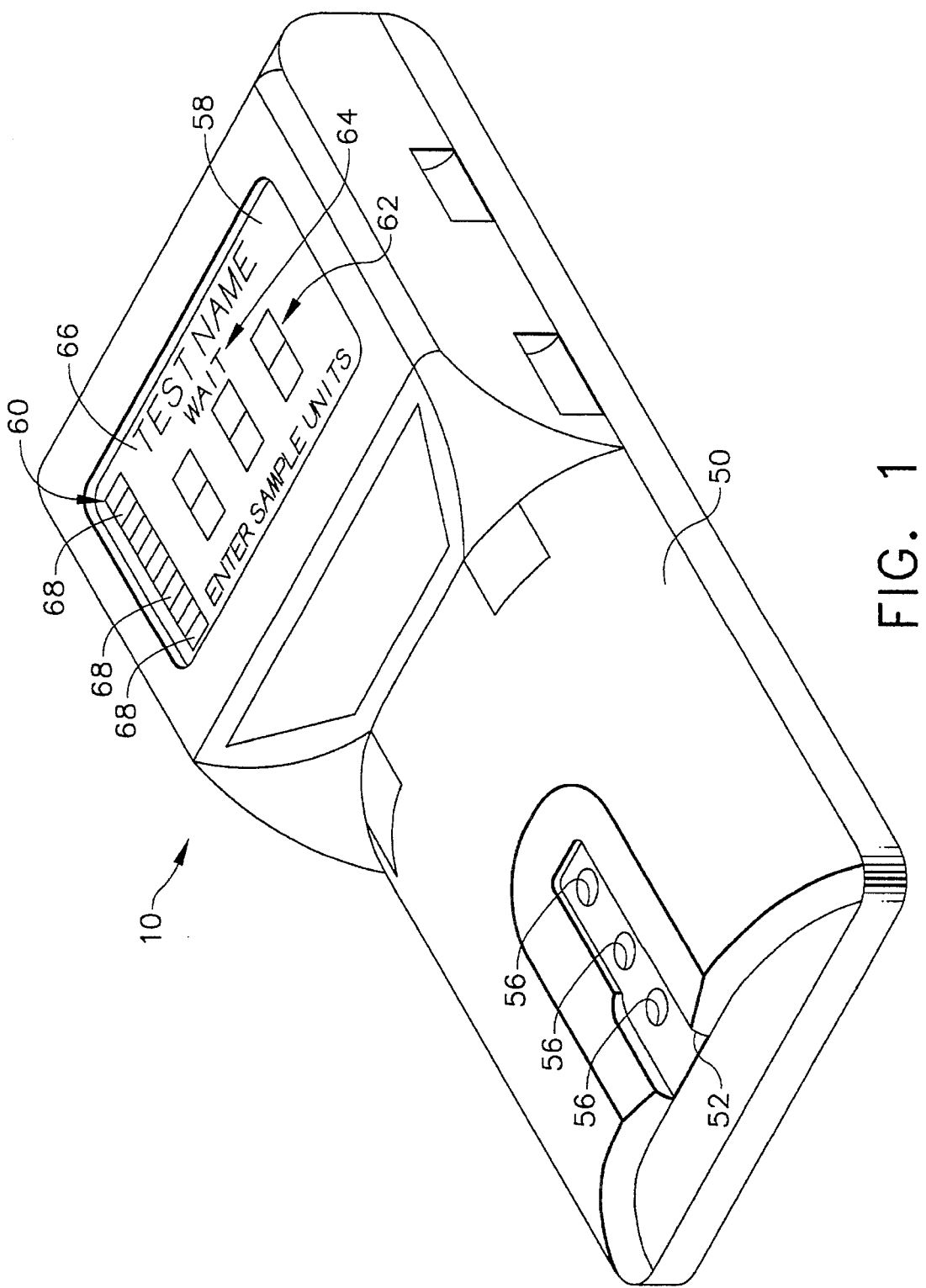
FIG. 1 is a perspective view of the reflectance photometer in accordance with an embodiment of the present invention.

The present invention also includes use of a spectrophotometric device 10 for determining the density of the color reaction on and in the membrane surface of the test reaction layer 32 within test strip 12. Photometric device 10 as shown in FIG. 1 includes a hand-held housing 50 for containing electronic control circuitry for operating the aforementioned tests. In the embodiment shown in FIG. 1, a test strip holding region 52 is located above three light detectors or sensors 54 each disposed within a port 56. During test operation, a test strip 12 is inserted into holding region 52 so that test strip openings 26 are located adjacent ports 56. Light sensors may take a reading from light reflected from the exposed test reaction membrane layer 32 or from test strip 12 itself to determine its color.

Housing 50 further includes a specialized display device, such as a liquid crystal display 58. Display 58 is utilized for relating test results and other information to the user. In particular, a color scale 60 is used to facilitate interpretation of test results operating concurrently with digital display segments 62. Additional display segments on display 58 include a test wait indicator segment 64 to inform the user to wait while device 10 is performing the selected tests, and a test name segment 66 which the unit determined from the type of test strip 12 inserted.

Color scale 60 may easily by constructed by a plurality of shaded or colored segments arranged adjacent each other to form a bar graph like indicator. Electrically controllable segments 68 are oriented over the color or shaded segments so that when segments 68 are activated segments 68 become dark, preventing certain colored or shaded segments 60 from being visualized or viewed. Segments 68 that are not activated permit the underlying colored or shaded segments of color scale 60 to be visualized. In this way it is possible for an electronic control to permit only a single colored or shaded segment to be viewed thereby communicating test results.

A possible result range spectrum for color scale indication segments may include particular colors with particular test result meanings such as:

Very high result danger, RED
high result danger, RED
high result caution, YELLOW
high result caution, YELLOW
high normal result, GREEN
normal result, GREEN
normal result, GREEN
low normal result, GREEN
low result caution, YELLOW
low result caution, YELLOW
very low result danger, RED Color scale 60 permits an unsophisticated user to instantly visually determine, in one embodiment, if a test result is normal (a green segment visualized), slightly abnormal (a yellow segment visualized) or dangerous high or low result (a red segment visualized). Alternatively, if a color liquid crystal display is utilized, the electronic control for test unit 10 may directly indicate a colored segment, rather than covering all but one colored segment.

Figure 5:
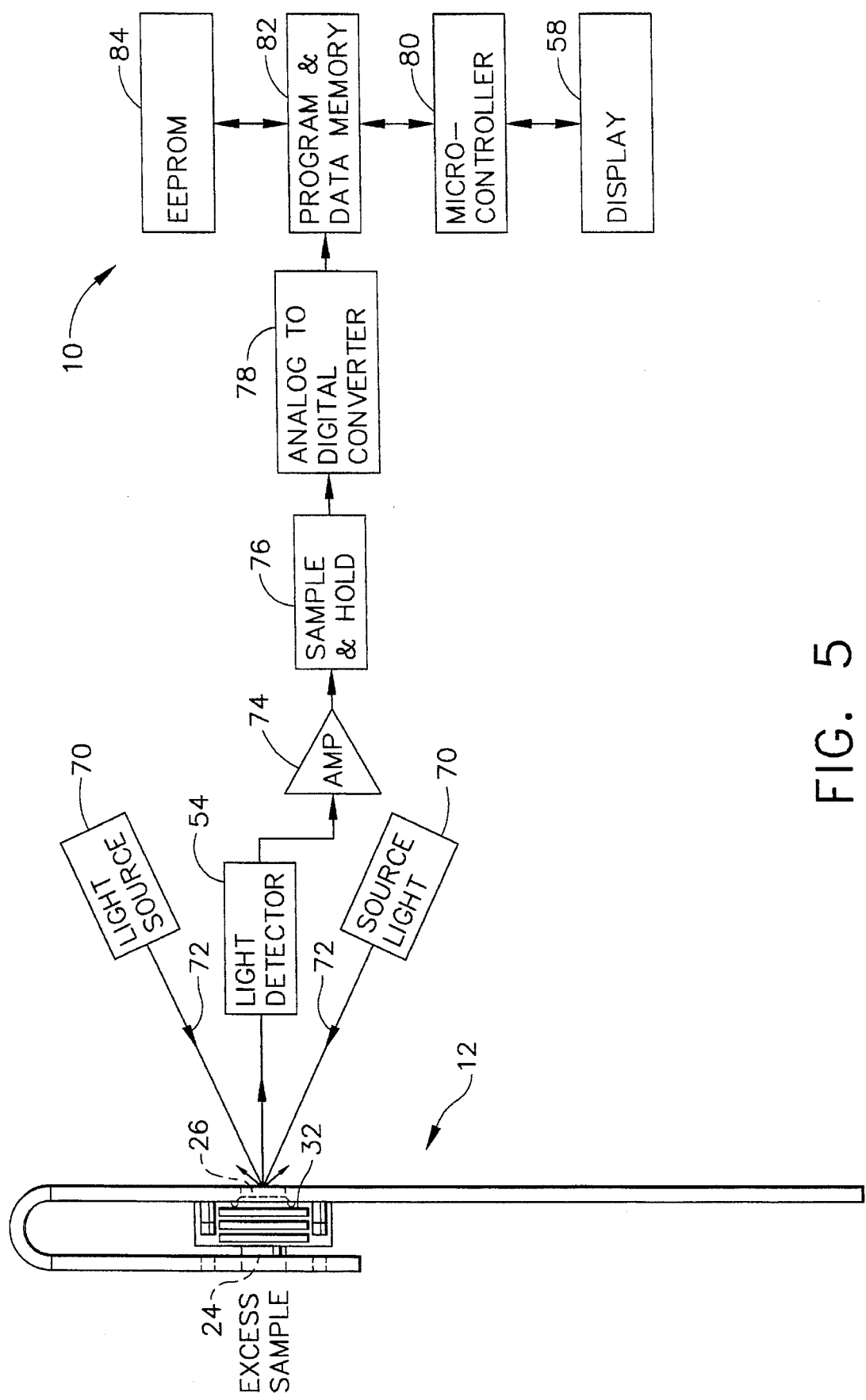
FIG. 5 is a block diagram schematic of one embodiment of the reflectance photometer of the present invention.

A suitable instrument, such as a diffuse reflectance spectrophotometer 10 with appropriate software, can be made to automatically read reflectance at certain points in time, calculate the rate of reflectance change, and by using calibration factors and software, output the level of analyte in the fluid tested. The electronic control mechanism of photometric unit 10 is shown in schematic form in FIG. 5. One or more light sources 70, for example high intensity light emitting diodes (LED) are disposed in housing 50 to illuminate test strip 12 as shown by arrows 72. A light detector or sensor 54, for example a photo transistor, is able to take a reading of light reflected either from the surface of test strip 12 or from its associated test reaction membrane 32. Light source 70 and light sensor 54 can be adapted to generate or respond to particular wavelengths of light.

Sensor 70 transmits a signal to an amplifier 74 as is known in the art. One type of amplifier available for use is, for example, a linear integrated circuit which converts the phototransistor current to a voltage signal.

Appropriate electronic Circuitry is utilized to take the output of amplifier 74, normally a sample and hold unit 76, and transfer the signal to an analog-to-digital converter 78. Analog-to-digital converter takes the analog voltage output from the sample and hold unit 76 and converts it to, for example a 16 bit binary digital number upon command of a microprocessor/microcontroller unit 80.

Preferably an electronic microprocessor/microcontroller 80 utilizing digital integrated circuitry is used to time selected tests, read signals, and together with associated programs and data memory 82, calculate and store reflectivity valves and calculate analyte levels from the stored data.

Additional information for particular tests may be stored in a removable EEPROM unit 84 operably connected to microprocessor/microcontroller 80. EEPROM unit 84 is an interchangeable plug-in memory module containing measurement parameters, software, calibration data, and reagent recognition data for particular test strips 12. Additionally, EEPROM unit 84 contains the shelf life data and identity verification information for particular production runs or lots of test strips 12.

Automated lot coding is done by the color coding the plastic material used to make the test strip holder 12. The color used in test strip holder 12 preferably has 16 different densities that can be distinguished by at least one of the wavelengths used in the optical sensor head 54 of instrument 10. For instance the dynamic range of the % reflectances of the strip holder color could be as follows to determine the different shades of color density:

| % Reflectance Green LED | % Reflectance Red LED | Lot # |
|---|---|---|
| 70 | | 1 |
| 65 | | 2 |
| 55 | | 3 |
| 50 | | 4 |
| 45 | | 5 |
| 40 | | 6 |
| 35 | | 7 |
| 30 | | 8 |
| | 70 | 9 |
| | 65 | 10 |
| | 60 | 11 |
| | 55 | 12 |
| | 50 | 13 |
| | 45 | 14 |
| | 40 | 15 |
| | 35 | 16 |

As the strips 12 are inserted into device 10, the instrument detects a change in the measurement area. This change indicates that a strip 12 has been inserted into the instrument 10. As the instrument detects the insertion of a test strip 12, it reads the densities of at least one of the LED's and calculates the lot number by the above table. Instrument 10 then goes to the EEPROM port connected to microprocessor/microcontroller 80 which has an EEPROM unit 84 inserted. Instrument 10 checks to see that the EEPROM preselected lot number is the same as lot number of test strip 12 that had been inserted into the instrument. If the lot numbers are the same for test strip 12 and EEPROM 84, the instrument downloads the information contained in the EEPROM and proceeds with the test analysis. The instrument 10 reads the density of the unreacted strip to assure quality of the strip before the test is initiated, if quality is passed then the instrument instructs the user to apply a sample.

A sample is then applied and instrument 10 begins a measurement cycle to ensure that the proper amount of sample was applied to the test strip. When the instrument has determined that enough sample has been applied, it then goes into another cycle to measure the end of the chemistry reaction. When the end of the chemistry reaction has occurred, then the instrument measures the final density and compares it to a measurement algorithm stored in EEPROM unit 84. This measurement algorithm then determines the concentration of the test to be measured by comparing the measured density (darkness) of the color formed and comparing this density number to a table of values through the use of an algorithm stored in the EEPROM unit 84.

After a particular test strip is selected and placed in the unit, a sample, normally a whole blood sample from a fingertip or from a pipiter tip (which could have gotten its sample from a tube of blood as in a laboratory type situation) is applied to the sample application spot, opening 24, on test strip 12. A dispersement layer 28 causes the sample to quickly spread over the entire area of carrier layer 14. The separation layer 30 of the test strip spot is allowed to separate out the solids (red blood cells and other analyte disrupting elements) from the liquid (plasma or sera or other analyte containing portion). The separated fluid, i.e the plasma, sera, or other analyte containing portions, moves to the test reaction membrane layer 32 below the separation membrane 30. The above fluid migration causes the reactants (analytes such as glucose) in the sample to come into contact with the reactants in test reaction membrane layer 32.

Analytes/fluid contacts reagent layer reaction 32 and initiates an appearance or disappearance of color, depending on its particular reaction. The above presentation of analyte to the reaction layer 32 causes the desired reaction to occur. This reaction causes a color change that can be detected both visually and by the instrument. The color change is then converted into a digital result on the instrument LCD as described above. A comparison color chart can be used to visually determine a reaction quantity scale as in litmus paper.

Instrument 10 can use different wavelengths at different density portions of the reaction to maximize the dynamic range of the chemistry and the limits of the instrument at a particular wavelength.

Figure 6:
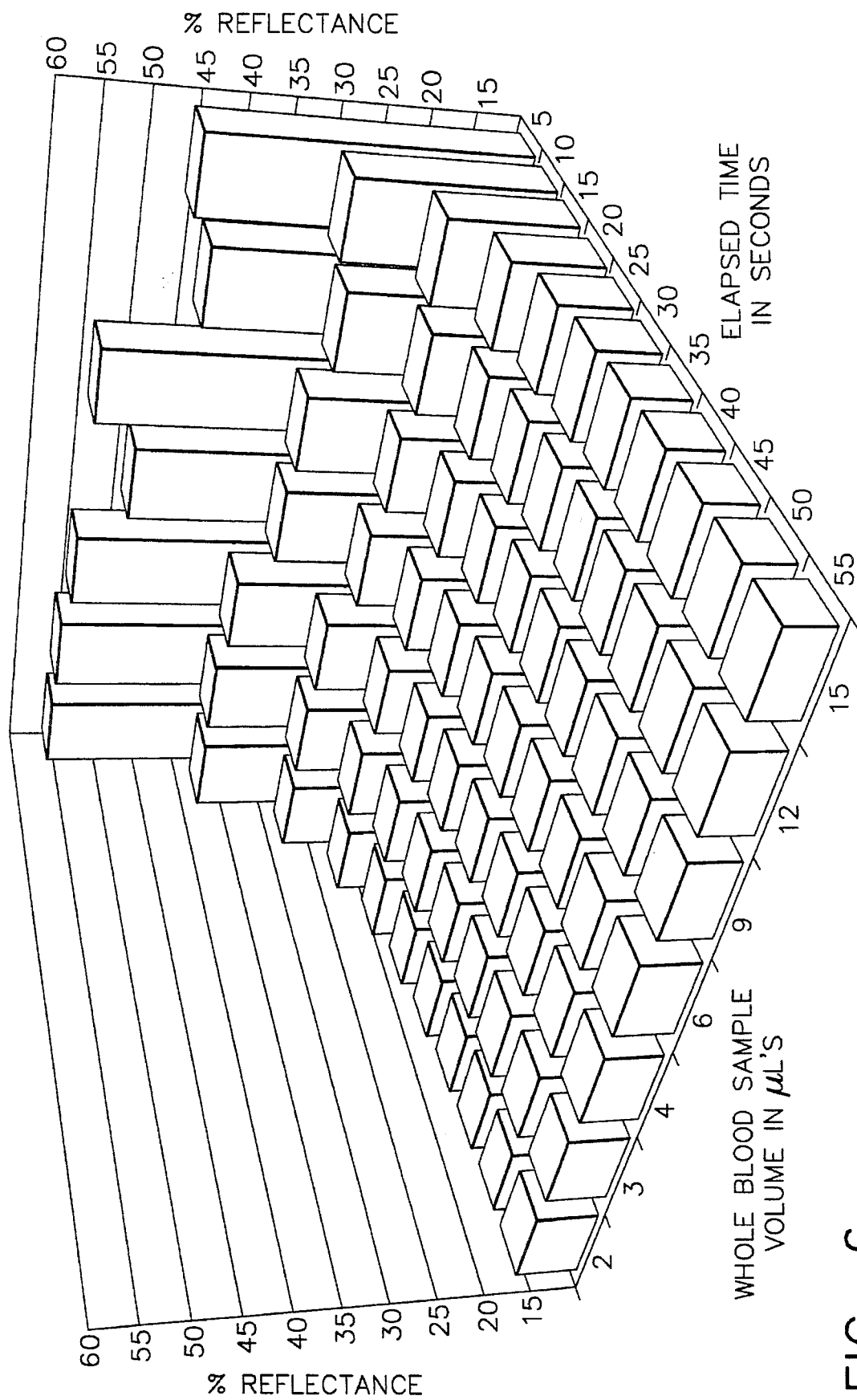
FIG. 6 is a graph plotting sample size, elapsed test time and percentage of reflectance illustrating how endpoint determinations may be utilized to speed chemistry measurement.

The "end-point" of the reaction is defined as a point where there appears to be no change or a very small change in density. That is, the chemistry changes color proportional to the concentration of the reactance that has come into contact with the reactance materials in the test pad (membrane). This small amount of change can be a change per time period. An example would be as per the graph in FIG. 6. Detailed information used to generate this graph is that the changes per 5 second time period during the beginning of the test reaction would be greater than 5% reflectance per 5 second time period. When this change is less than 1% reflectance per time period it can be said that the reaction is complete or at an endpoint. The instrument stores this percentage reflectance at this time and uses as above to determine the concentration of the analyte tested for in the test strip.

The Kubelka-Monk equation of $K/S=(1-\text{reflectance})^2$ divided by $(2\times\text{reflectance})$ can be used to linearize the percentage reflectance values. This linearization simplifies the algorithm necessary to calculate results. This pseudo endpoint chemistry allows a more stable read time, which in turn allows for a more reproducible answer. Pseudo endpoints also permit a more rapid assay to be performed. Certain other glucose monitoring systems incorporate predetermined timing circuit. This pseudo endpoint allows for a different method to be used in measuring chemistry reactions, provided one can determine the endpoint of the chemistry by a method other than timing.

Multiple wavelengths are used to enhance the dynamic range of a chemistry. This is particularly useful when one uses a multiple chromophore indicator system as do some of the above mentioned chemistries. Early portions or low concentrations of a test such as glucose can use a broad range indicator such as TMB to increase sensitivity in the low to mid range of the chemistry. When the test concentration is higher or the reaction faster, a different chromophore is focused upon to determine more dynamic range than the previous chromophore. This allows one to expand the dynamic range by two different methods.

One can also use wavelengths on the peak for more dynamic range and wavelengths off the "peak" absorbance of the test system to enhance or reduce dynamic range and also to enhance or reduce the "pseudo endpoint" algorithms. Manipulation of these four factors, chromophore A, chromophore B, wavelength 1 and wavelength 2 can allow one to better define the "pseudo endpoint" algorithm and also allow one to optimize the dynamic range of the chemistry which in turn allows for increased sensitivity throughout the chemistry reaction range with greater precision.

Multiple wavelengths can also be used with different angles of emission to correct possible problems in positioning the strip in the instrument. If the detector is at "0" angle and the emitters of the same or different wavelengths are at different angels (one at 40° and one at 50°) the tilting of a surface will positively contribute to one reading while the other contributes in a negative manner thus cancelling the error presented by the angle presentation of the surface. These same measurements methods can be used to eliminate interferences from substances such as bilirubin and others. When the angle of light incidence is increased from improper positioning of a chemistry read surface to the instrument optics, errors of both gloss and angularity are introduced into the measuring system and can give false low readings.

EXAMPLES

1. Indicators and chromogens advantageously used in combination
   a. wide range pH test
   Bromothymol blue and methyl red covers pH range of 5 through 9
   b. 4 amino antipyrine+3,5 dichlorohydroxybenzene sulfonate (4AAP+3,5 DCHBS)
   c. TMB+Chromotropic acid
   d. Syringaldazine+Vanillin Azine
2. Color coding for test and lot identification
   a. blues, 16 different shades (density)

b. reds, 16 different shades (density)
c. greens, 16 different shades (density)
d. yellows, 16 different shades (density)
e. ranges, 16 different shades (density)
f. browns, 16 different shades (density)
g. magentas, 16 different shades (density)
h. light blues, 16 different shades (density)
i. light reds, 16 different shades (density)
j. light greens, 16 different shades (density)
k. light browns, 16 different shades (density)
l. light magentas, 16 different shades (density)
m. cyan, 16 different shades (density)
n. light cyan, 16 different shades (density)

It will be appreciated that the foregoing is presented by way of illustration only, and not by way of any limitation, and that various alternatives and modifications may be made to the illustrated embodiment without departing from the spirit and scope of the invention.

What is claimed is:

1. A diagnostic test strip for use in an analyzer for measuring analyte in a sample, said test strip comprising:

an elongate body including a first end, a second end, and a hinged portion between said first and second ends, said first end being foldable over said second end, said first end and said second end each having an opening that is aligned with one another when said first end is folded over said second end; and a single carrier layer means comprising a plurality of layers fixed in position without use of adhesives between said openings within said first end and said second end, said carrier layer means including a separating layer that when exposed to a whole blood sample excludes red blood cells from passing therethrough while allowing the liquid portion of the whole blood sample to pass therethrough, whereby a sample communicated to said carrier layer means is prevented from pooling within said carrier layer means.

2. The test strip of claim 1 having a carrier layer means utilizing samples in the range of 2.0ul to 10.0ul to generate a reaction to accurately test a selected analyte.

3. The test strip of claim 1 in which said carrier layer means includes:

a separating layer that when exposed to a sample liquid having both analytes and analyte disrupting elements said separating layer excludes said analyte disrupting elements from passing therethrough while allowing the analyte portion of the sample liquid to pass therethrough; and a test reaction membrane layer adjacent said separating layer that creates a gradient color dependant on the concentration of selected analytes in the analyte portion that had passed through said separating layer.

4. The test strip of claim 1 in which said carrier layer means includes a spreading layer over said separating layer to cause sample to substantially evenly enter said separating layer.

5. The test strip of claim 1 in which said carrier layer means may test more than one analyte at one time.

6. The test strip of claim 1 in which said second end includes a locking means lock together said first end and said second end.

7. The test strip of claim 1 further comprising a tab and an opening one of which on said first end the other on said second end so that when said first end folds into contact with said body, said tab interfits with said opening to lock said first end with said body.

8. The test strip of claim 1 wherein said first and second ends each contain a second opening which is aligned with one another when said first end is folded over said second end.

9. The test strip of claim 1 wherein said carrier layer means contains up to eight layers fixed in position.

10. The test strip of claim 1 wherein said strip is color coded for identification of a particular chemical test for which said strip is operable.

11. The test strip of claim 10 wherein the color of said strip is composed of one of sixteen different densities which are distinguishable by an optical sensor.

12. A diagnostic test strip for use in an analyzer for measuring analyte in a sample, said test strip comprising:

an elongate body including a first end, a second end, and a hinged portion between said first and second ends, said first end being foldable over said body, said first end and said second end each having an opening that are aligned when said first end is folded over said body;

carrier layer means comprising a plurality of layers disposed adjacent each other and held together between the openings within said first end and said second end of said body without the use of an adhesive whereby the accuracy of measure analyte is increased, said carrier layer means including a separating layer which is treated with light metal salts to reduce red blood cells in the sample; and means holding said carrier layer means in a fixed position between said first end and said body whereby pooling of sample within said carrier layer means is prevented.

13. The test strip of claim 12 in which said holding means comprise protrusions to locate said carrier a layer means in place whereby said carrier layer means is maintained in known locations along the X, Y and Z axes.

14. The test strip of claim 12 in which said holding means comprise sawtooth protrusions to locate said carrier layer means in place whereby said carrier layer means is maintained in known locations along the X, Y and Z axes.

15. The test strip of claim 12 wherein said first end and said second end each contain a second opening which are aligned when said first end is folded over said body.

16. The test strip of claim 12 wherein said carrier layer means contains up to eight layers held together between said openings.

17. The test strip of claim 12 wherein said strip is color coded for identification of a particular chemical test for which said strip is operable.

18. The test strip of claim 12 wherein the color of said strip is composed of one of a plurality of different densities which are distinguishable by an optical sensor.

19. The test strip of claim 18 wherein said strip is composed of one of up to sixteen different densities.

20. A diagnostic test strip for use in an analyzer for measuring analyte in a sample, said test strip comprising:

an elongate body including a first end, a second end, and a hinged portion between said first and second ends, said first end being foldable over said body, said first end and said second end each having an opening that are aligned with one another when said first end is folded over said body;

carrier layer means comprising a plurality of layers disposed adjacent each other and held together between the openings within said first end and said second end of said body without the use of an adhesive whereby the accuracy of measured analyte is increased, and means holding said carrier layer means in a fixed position between said first end and said body, said first end folding over said carrier layer means and locking to said body causing the layers of said carrier layer means to be in adjacent contact without adhesives thus effecting efficient separation of red blood cells from plasma in whole blood samples and whereby pooling of sample within said carrier layer means is prevented.

* * * * *